United States Patent [19]

Huene

[11] Patent Number: 4,869,243
[45] Date of Patent: Sep. 26, 1989

[54] DEVICE AND METHOD FOR JOINING FRACTURED BONES

[76] Inventor: Donald R. Huene, 201 N. Valeria, Fresno, Calif. 93701

[21] Appl. No.: 161,081

[22] Filed: Feb. 26, 1988

[51] Int. Cl.⁴ ........................ A61F 5/04; A61B 17/04
[52] U.S. Cl. ............................ 128/92 R; 128/92 YC; 128/92 YE; 128/334 R; 227/DIG. 1
[58] Field of Search ................ 128/92 R, 337, 334 R, 128/335, 92 YC, 92 YE; 227/19, 20, 21, DIG. 1 SC

[56] References Cited

U.S. PATENT DOCUMENTS

| | | | |
|---|---|---|---|
| 3,098,232 | 7/1963 | Brown | 128/334 R |
| 3,232,089 | 2/1966 | Samuels | 128/334 R |
| 3,586,002 | 6/1971 | Wood | 227/DIG. 1 SC |
| 4,256,251 | 3/1981 | Moshofsky | 128/334 R |
| 4,391,401 | 7/1983 | Moshofsky | 227/19 |
| 4,391,402 | 7/1983 | Campbell | 128/334 R |
| 4,399,810 | 8/1983 | Samuels et al. | 128/337 |
| 4,414,967 | 11/1983 | Shapiro | 128/92 VT |
| 4,470,532 | 9/1984 | Froehlich | 227/19 |
| 4,485,816 | 12/1984 | Krumme | 227/DIG. 1 SC |
| 4,505,273 | 3/1985 | Braun et al. | 128/335 |
| 4,550,870 | 11/1985 | Krumme et al. | 227/19 |
| 4,582,237 | 4/1986 | Storace et al. | 227/19 |
| 4,591,086 | 5/1986 | Campbell | 128/334 R |
| 4,619,262 | 10/1986 | Taylor | 128/334 R |
| 4,619,391 | 10/1986 | Sharkany et al. | 227/19 |
| 4,655,222 | 4/1987 | Florez | 128/334 R |

Primary Examiner—Robert A. Hafer
Assistant Examiner—Michael Brown
Attorney, Agent, or Firm—Shlesinger & Myers

[57] ABSTRACT

A crimper and method for drawing together two bone fragment. The crimper includes a support member having an adjustable fulcrum and a clamping device for holding a staple or an elongated member. A forming die member operable in a recess of the support member engages with a portion of the staple or elongated member which extends in the recess. The forming die member includes a fulcrum point which is movable on the adjustable fulcrum. The forming die member is movably secured to the support member and includes a lever arm on one side of the fulcrum point and a forming die on the other side of the fulcrum point. The lever arm includes a device for moving the forming die member about the fulcrum point. During use, when the forming die member is operated, the forming die applies a pressure on the staple or elongated member to form a crimp in a portion thereof which extends through the recess.

60 Claims, 2 Drawing Sheets

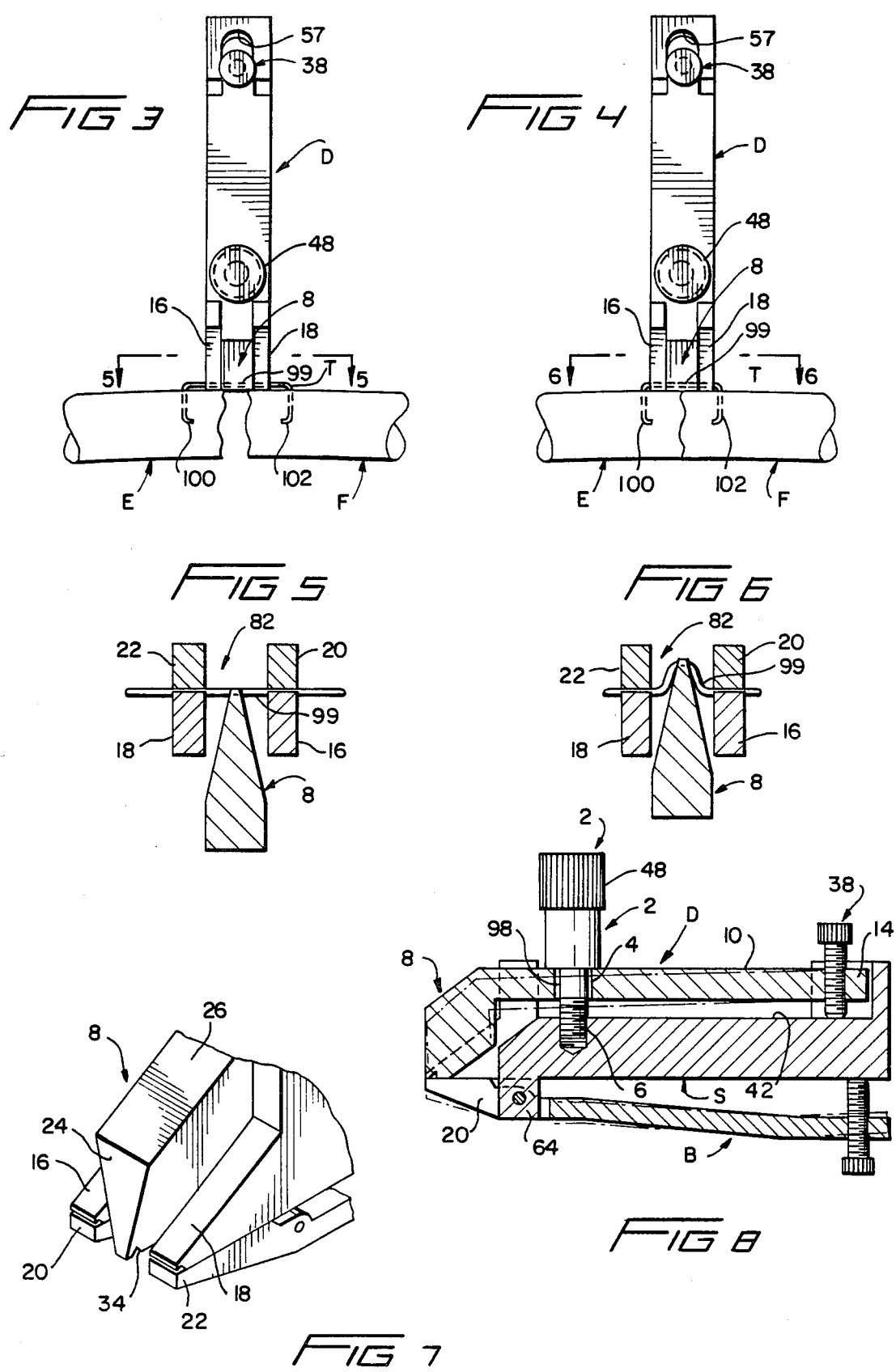

DEVICE AND METHOD FOR JOINING FRACTURED BONES

BACKGROUND AND FIELD OF INVENTION

The present invention relates to a device and method for drawing together two bones or the like, particularly bones separated by a fracture.

Conventionally, fractured bone fragments, wounds, lacerations and incisions in the skin are closed by implanting surgical staples. Various surgical stapling devices have been developed to achieve this objective. In use, the tissue or the bone fragments to be joined together are placed side by side or moved closer together, and a surgical stapling device is used to drive a staple into the fragmented portions for holding the fragments in place until the wound is sufficiently healed or, for example, the bone fragments have fused together by the body's healing mechanism. Once the healing or fusion of the components is complete, the staple may then be taken out by using another device. The prior art is replete with surgical stapling devices which can be used to attain this objective. Prior art patents which disclose surgical stapling devices are U.S. Pat. Nos. 4,391,401, 4,399,810, 4,470,532, 4,550,870, 4,582,237, 4,619,262, and 4,619,391. U.S. Pat. Nos. 4,505,273 and 4,655,222 disclose the types of staple that may be used in a surgical stapling device for closing or suturing a wound or incision, and the U.S. Pat. No. 4,414,967 discloses a method of joining bone to bone tendon, and ligament to bone by using a power staple gun or rivet gun.

However, as it is known, it is critical that the two fragments which are to be joined, be aligned properly with respect to each other so that when the fusion between them takes place, the fragments join or fuse substantially in a position resembling the position of a natural, unbroken or unfractured fragment. For example, when two bone fragments are to be joined, the fragments are placed close together and a staple is then hammer or power driven into the fragments. However, due to the hammering action there is a substantial likelihood that the fragments would move from their initial position and an improper fusion of the fragments will take place. In addition, often a staple remains firmly affixed to the stapling device and thus it becomes a pain-staking process to remove it from the bone fragments of the patient.

OBJECTS AND SUMMARY OF THE INVENTION

Accordingly, it is one object of the invention to provide a device for drawing two components together for their precise fusion.

Another object of the present invention is to provide a device for drawing two components together which is simple in construction and easy to use.

A further object of the invention is to provide a device for drawing two components together which causes a staple to be crimped thereby pulling the two fragments together.

A still further object of the invention is to provide a device for drawing two components together which crimps a staple in a direction transverse to the direction of the legs of the staple.

Another object of the present invention is to provide a device for drawing two components together whereby the staple is easily removed from the device once the staple has been inserted into the fragments and/or crimped.

A further object of the present invention is to provide a device for drawing two components together in a tight constant pressure fit not previously possible and particularly in the case of bone surgery. Such tight fit with pressure aids in speeding healing of the fracture much faster than any present system available.

A still further object of the present invention is to provide a device for drawing two components together which can be used to place a crimp of a varying depth in a staple which allows the doctor to visually judge how tight he wants the abutting members to be without structural damage to the bone fractured ends.

Another object of the present invention is to provide a method for drawing bone fragments together.

A further object of the present invention is to produce a staple which has a crimp extending in a direction transverse to the direction of the legs.

In summary, the present invention provides a method for drawing two components together, in particular, bone fragments.

These and other objects and other advantages of the invention will be readily apparent in view of the following description and drawings of the above described invention.

DESCRIPTION OF THE DRAWINGS

The above and other objects and advantages and novel features of the present invention will become apparent from the following detailed description of the preferred embodiment of the invention illustrated in the accompanying drawings, in which:

FIG. 3 is a top plan view of the device of the present invention in operation before crimping a staple;

FIG. 4 is a top plan view of the device of the present invention in operation wherein the staple has been crimped and the two fragments are drawn closer;

FIG. 5 is a partial front-elevational view taken along line 5—5 of FIG. 3 showing the staple in place prior to being crimped;

FIG. 6 is a partial front-elevational view taken along line 6—6 of FIG. 4 showing the staple being crimped;

FIG. 7 is an enlarged perspective view of the device showing the front portion thereof; and FIG. 8 is a longitudinal cross-sectional view of the device of the present invention.

DESCRIPTION OF THE INVENTION

Figure 1:
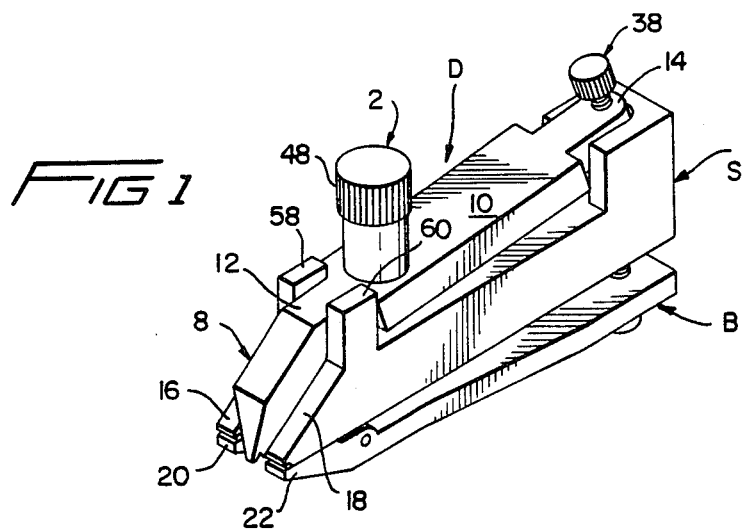
FIG. 1 is a perspective view of the device of the present invention.
Figure 2:
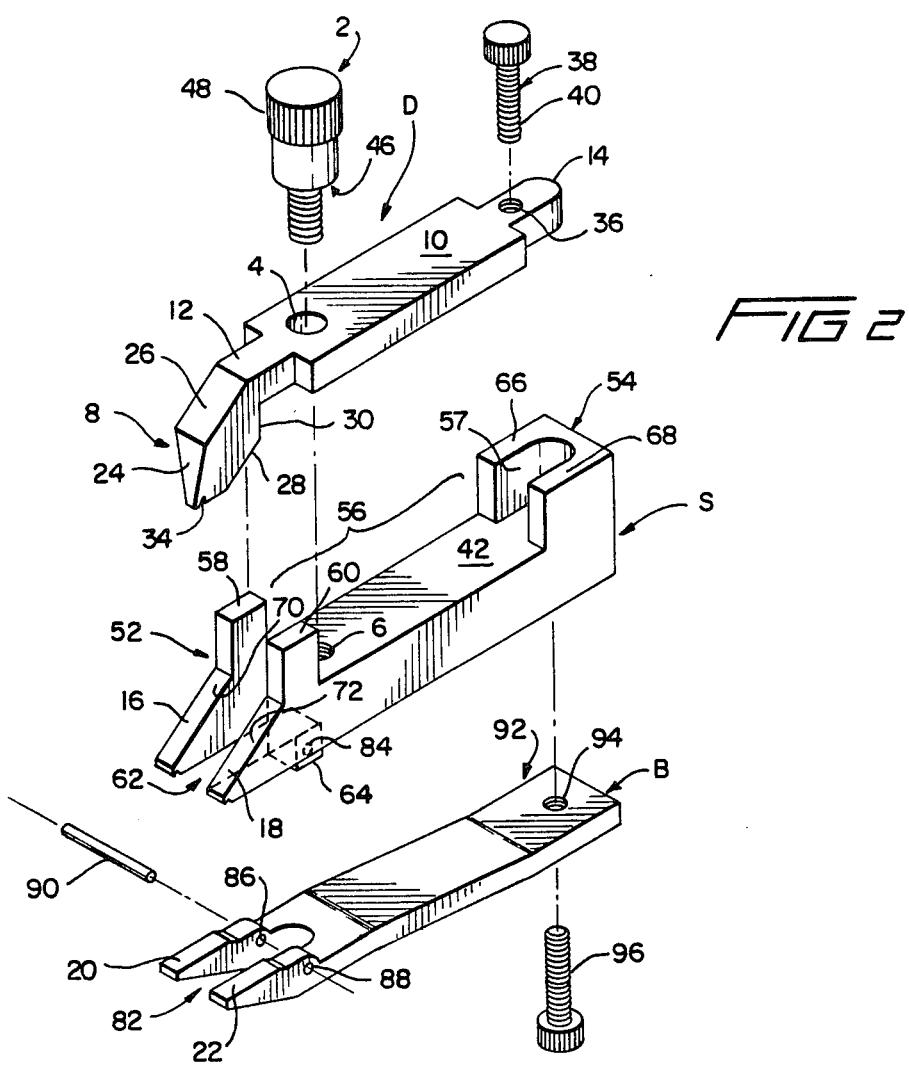
FIG. 2 is an exploded view of the device of the present invention as shown in FIG. 1.

As shown in FIGS. 1 and 2, the crimper of the present invention includes a forming die member D which is supported on a support member S and a base plate B. Forming die member D is pivotally attached to support member S by an adjustable fulcrum screw member 2, which passes through a hole 4 in the forming die member D and is received into a screw-threaded hole 6 in the support member.

Forming die member D includes a forming die or head 8, which is connected to a body portion 10 by a neck portion 12. A tail portion 14, which has a width less than that of a body portion 10, is connected to the body portion 10. The head 8 extends and is operable in a space defined by laterally spaced jaws 16 and 18 of the support member S and laterally spaced jaws 20 and 22 of the base plate B. The head 8 is polygonal in shape and includes two surfaces 24 and 26 and two oppositely disposed lower surfaces 28 and 30 as best shown in FIG. 2. The head 8 further includes a tip 32, which connects the upper surface 24 with the lower surface 28. A groove 34 running transverse to a general longitudinal axis of the crimper C, is provided on the tip 32 for holding a portion of a staple T.

The tail portion 14 has a screw-threaded hole 36 for receiving a lever or moving screw 38 therein. When the forming die member D is placed on top of the support member S, the shank 40 of screw 38 passes through screw-threaded hole 36 and contacts a upper surface 42 of the supporting member S. Similarly, a shank 44 of adjustable fulcrum screw member 2 passes through a hole 4 in the body portion 10 of the forming die member D and is received in screw-threaded hole 6. Accordingly, as shown in FIGS. 1 and 8, forming die member D rocks or pivots about a fulcrum point 46 (FIG. 2). As shown in FIG. 2, the head 48 of adjustable fulcrum screw 2 is enlarged and may be knurled as shown or smooth. Head 50 of screw 38 is knurled for better gripping and more positive pressure.

Support member S includes a proximal portion 52 (FIG. 2), a distal portion 54, and an open space 56 defined by the proximal and distal portions 52 and 54. As shown in FIG. 2, distal portion 54 has a generally "horse-shoe" shaped upwardly extending extension 57 which defines a space therein for receiving the tail portion 14 of forming die member D. The proximal portion 52 of support member S includes two laterally spaced shoulders 58 and 60 in front of each of which extends laterally spaced upper jaws 16 and 18, respectively. The laterally spaced upper jaws 16 and 18 and shoulder portions 58 and 60 together define a space 62 (FIG. 2) therebetween for receiving the head 8 of the forming die member D. A leg or foot 64 extends away from the shoulders 58 and 60, and is provided on the lower surface of support member S. The shoulders 58 and 60 and the arms 66 and 68 of the "horse-shoe" shaped extension 57 define an open space 56 to receive the body portion 10 of the forming die D. The length and breadth of the body portion 10 corresponds to the length and breadth of the open space 56.

Laterally spaced upper jaws 16 and 18 include downwardly inclined surface 70 and 72 which terminates in vertically extending edges 74 and 76. The laterally spaced upper jaws 16 and 18 include grooves 78 and 80 respectively, which run substantially transverse to a general longitudinal axis lying about a central vertical plane of the crimper C.

The leg 64 is received into a space 82 defined by the lower jaws 20 and 22 for pivotally connecting the support member S with the base member B.

The base plate B, as mentioned above, includes a pair of laterally spaced lower jaws 20 and 22, which together with upper jaws 16 and 18 hold a staple T. The leg 64 of the support member S includes transversely extending hole 84 (FIG. 2). Each of the lower jaws 20 and 22 includes a transversely extending hole 86 and 88, respectively, such that when the support member S is placed on top of the base plate B and leg 64 is received in the space 82, a pin-shaped member 90 passes through holes 86 and 88 and through hole 84 of the leg 64. A posterior portion 92 of base plate B has a screw-threaded hole 94 through which a grip-adjustment screw member 96 extends and applies pressure on the bottom of support member S.

As shown in FIG. 7, groove 34 of the forming die member D and grooves 78 and 80 of upper jaws 16 and 18, respectively, are aligned such that they together form a transversely extending axis about which a staple or pin-shaped member T may be positioned so that a downward pressure may be applied by pivoting the head 8 of the forming die member D.

A crimper C including forming die member D, support member S, and base plate B, could be made of a suitable light-weight metal material, such as aluminum, or be made of plastic. However, it should be noted that it would be apparent to those of ordinary skill in the art, that various components of the present device could be made of a metal or a sufficiently strong material other than a metal.

OPERATION

In operation, a staple or pin-shaped member T is positioned between the upper and lower jaws 16 and 18 and 20 and 22, respectively in the grooves 78 and 80 of the support member S.

As best shown in FIG. 8, when the grip adjustment screw 96 is actuated to exert a pressure on the lower side of the support member S, the base plate B will pivot about an axis of pin 90, and the lower jaws 20 and 22 will be locked with the upper jaws 16 and 18. Therefore, the staple or pin-shaped member T is firmly held between the upper and lower jaws 16 and 18 and 20 and 22 by actuating the grip-adjustment screw member 96. Once the staple or pin-shaped member T is held in place in the grooves 78 and 80, the head 8 of forming die member D is brought into contact with the staple or pin-shaped member T such that groove 34 of forming die member D clamps a portion of staple or pin-shaped member T. The clamping of the staple or pin-shaped member T in groove 34 is carried out by adjusting the position of the fulcrum point 46 by screwing the adjustable fulcrum screw 2 into screw-threaded hole 6 in the support member S. In this position, screw member 38 maybe left in a totally unscrewed position such that it is not exerting any downward pressure on the upper surface 42 of the support member S, or is exerting a minimum or negligible pressure thereon. As shown in FIGS. 1 and 8, the hole 4 in the forming die member has a slightly larger diameter than the diameter of the smooth neck portion 98 of the adjustable fulcrum screw 2. This construction allows fulcrum screw 2 to float or freely slide in hole 4. Accordingly, when screw 38 is tightened/screwed to exert a downward pressure on the support member S, the forming die member D rocks or pivots about a fulcrum point 46. The pivoting or rocking motion of the forming die member D about fulcrum point 46 causes the head 8 to place a downward pressure on the staple T thereby causing it to crimp.

As shown in FIG. 3, the staple T is first inserted into the two bone fragments E and F to be drawn closer and the crimper C of the present invention is positioned so as to hold the central portion 99 of the staple T between the upper and lower jaws 16, 18, 20 and 22. The head 8 of the forming die member D is positioned on the staple T by adjusting the position of the adjustable fulcrum screw member 2. The crimper C securely holds the staple, and the moving screw member 38 is then screwed into its corresponding hole 36 to place a pressure on support member S. The continued screwing motion of moving screw member 38 causes the forming die member D to pivot (rock) about the fulcrum point 46, which in turn causes the head 8 to place a downward pressure on the staple T to thereby crimp it, as shown in FIG. 6. As shown in FIG. 4, the crimp, which extends transverse to the direction of staple T's legs causes the legs of the staple to come closer, and thereby, draws the two bone fragments C and D closer as well.

The device of the present invention is particularly advantageous in that the actuation of moving screw 38, brings the bone fragments E and F together to a degree as determined by the doctor and further allows manipulation of the bone fragments E and F to make certain that the fragments E and F are aligned properly.

While this invention has been described as having a preferred design, it is understood that it is capable of further modifications, uses, and/or adaptations of the invention and following in general the principle of the invention and including such departures from the present disclosure as has come within known or customary practice in the art to which the invention pertains, and as may be applied to the central features hereinbefore set forth, and fall within the scope of the invention of the limits of the appended claims.

What I claim is:

1. A crimper, comprising:
  (a) supporting means for supporting an elongated member;
  (b) said supporting means including an adjustable fulcrum;
  (c) said supporting means including clamping means for holding the elongated member;
  (d) said supporting means including a recess through which a portion of the elongated member extends;
  (e) forming die means operable in said recess and engageable with said portion of the elongated member in a direction transverse to the axis of the elongated member;
  (f) said forming die means being movable secured to said supporting means;
  (g) said forming die means including a fulcrum point movable on said adjustable fulcrum;
  (h) said forming die means including a lever arm on one said of said fulcrum point and a forming die on the other side of said fulcrum point;
  (i) said lever arm including means for moving said forming die means about said fulcrum point;
  (j) said lever arm comprising a substantially planar body portion, and a tail portion;
  (k) said forming die comprising a head portion connected to said body portion by a neck portion;
  (l) said head portion extending substantially at right angle to the plane of said neck portion;
  (m) said head portion being substantially polygonal in shape and one surface thereof including a groove for receiving a portion of the elongated member;
  (n) the crimper including a generally longitudinal axis extending about a central vertical plane thereof;
  (o) said groove running transverse to said longitudinal axis of the crimper;
  (p) said adjustable fulcrum including a fulcrum screw member;
  (q) said fulcrum screw member comprising a head portion, a screw-threaded portion, and a neck section disposed between said head portion and said screw-threaded portion;
  (r) said body portion of said lever arm including a first hole slidably receiving said neck section of said screw; and,
  (s) whereby when said means for moving said forming die means is operated, said forming die applies a pressure to the elongated member to form a crimp in said portion of the elongated member extending in said recess.

2. The crimper of claim 1, wherein:
  (a) each of said neck portion of said lever arm, said body portion, and said tail portion having a length and a width.

3. The crimper of claim 2, wherein:
  (a) the width of said body portion being greater than the width of each of said neck portion and said tail portion.

4. The crimper of claim 3, wherein:
  (a) said means for moving said forming die means comprising a moving screw member;
  (b) said tail portion including a second hole for receiving said moving screw member;
  (c) said tail portion having a thickness; and,
  (d) said second hole running through said thickness of said tail portion thereby allowing said moving screw member to pass therethrough and contact a corresponding portion of said supporting means.

5. The crimper of claim 4, wherein:
  (a) said supporting means comprising a support member and a base plate disposed under said support member.

6. The crimper of claim 5, wherein:
  (a) said support member comprising a proximal portion, a distal portion, and a middle portion having an open space defined by said proximal and said distal portions; and,
  (b) said open space receiving said body portion of said lever arm when said forming die means is placed atop said support member.

7. The crimper of claim 6, wherein:
  (a) said middle portion of said support member comprising a screw-threaded hole located adjacent said proximal portion; and,
  (b) said screw-threaded hole corresponding to said first hole in said body portion of said lever arm such that a portion of said screw-threaded portion of said fulcrum screw member is received therein.

8. The crimper of claim 6, wherein:
  (a) said distal portion defining a recess substantially corresponding in shape to the shape of said tail portion of said forming die means.

9. The device of claim 6, wherein:
  (a) said proximal portion comprising a pair of vertically extending shoulders; and,
  (b) said shoulders being spaced apart such that said neck portion of said forming die means slides vertically therebetween.

10. The device of claim 9, wherein:
  (a) said clamping means comprising spaced jaws; and,
  (b) said spaced jaws comprising a first pair of jaws and a second pair of jaws cooperating with said first pair of jaws.

11. The crimper of claim 10, wherein:
  (a) said first pair of jaws being disposed in front of said shoulders;
  (b) said first pair of jaws each including a groove; and,
  (c) said groove running transverse to said longitudinal axis of the crimper.

12. The crimper of claim 10, wherein:
  (a) said support member comprising attaching means for attaching said base plate thereto.

13. The crimper of claim 12, wherein:

(a) said attaching means comprising at least one leg; and,
(b) said at least one leg being positioned adjacent said proximal portion and extending in a direction opposite to said shoulders.

14. The crimper of claim 13, wherein:
(a) said at least one leg having a transversely extending hole receiving a pin therethrough.

15. The crimper of claim 14, wherein:
(a) said base plate comprising an anterior portion, a central portion, and a posterior portion; and,
(b) said posterior portion including at least one screw-threaded aperture.

16. The crimper of claim 15, wherein:
(a) said anterior portion including said second pair of jaws defining a space therebetween; and,
(b) each of said second pair of jaws including a transversely extending hole receiving a portion of said pin therethrough such that when said support member is placed atop said base plate, said at least one leg is pivotally received in said space.

17. The crimper of claim 16, further comprising:
(a) at least one grip adjustment screw means for adjusting a grip of said elongated member between the first pair of jaws and said second pair of jaws; and,
(b) said at least one grip adjustment screw means being received in said at least one screw-threaded aperture in said posterior portion of said base plate.

18. A crimper, comprising:
(a) a forming die member comprising a head portion having a tip, and a substantially planar body portion;
(b) said head portion extending generally at right angle to the plane of said body portion;
(c) said head portion including a transversely extending groove on said tip for receiving a portion of an elongated member;
(d) a support member pivotally supporting said forming die member;
(e) said support member including an adjustable fulcrum screw member;
(f) said forming die member including a fulcrum point movable on said adjustable fulcrum screw member;
(g) said support member comprising a first pair of laterally spaced jaws;
(h) said first pair of jaws defining a space therebetween for receiving said head portion of said forming die member;
(i) a base plate member pivotally connected to said support member;
(j) said base plate member comprising a second pair of laterally spaced jaws cooperating with said first pair of jaws;
(k) a moving screw member operably associated with said forming die member for applying a pressure on said support member thereby pivoting said forming die member about said fulcrum point; and,
(l) a grip adjustment screw member operably associated with said base plate for applying a pressure on said support member to thereby grip said elongated member between said first pair and said second pair of jaws.

19. The crimper of claim 18, wherein:
(a) said forming die member comprising a plurality of holes, a first one of said holes located adjacent said head portion receiving said adjustable fulcrum screw member therein, a second one of said holes located away from said head portion receiving said moving screw member therein.

20. The crimper of claim 19, wherein:
(a) said support member comprising a screw-threaded hole corresponding to said first hole such that a portion of said adjustable fulcrum screw member is received therein.

21. The crimper of claim 20, wherein:
(a) said support member comprising a leg member pivotally securing said support member to said base plate member.

22. The crimper of claim 18, wherein:
(a) the crimper including a generally longitudinal axis extending about a central vertical plane thereof; and,
(b) at least one of said first pair of jaws including a groove extending transverse to said longitudinal axis of the crimper holding a portion of the elongated member.

23. The device of claim 18, wherein:
(a) said base plate member comprising a screw-threaded hole receiving said grip adjustment screw member therein.

24. A method of drawing bone fragments together, comprising the steps of:
(a) providing a generally staple-shaped member, the staple-shaped member having laterally spaced legs connected by a joining member;
(b) stapling the bone fragments such that one leg of said staple is positioned in one fragment and the other leg of said staple is positioned in the other fragment;
(c) connecting a crimping device to said joining member; and,
(d) crimping said joining member in a direction generally transverse to a plane in which at least one of said legs extends.

25. A crimped staple produced in accordance with a method, comprising the steps of:
(a) providing a generally staple-shaped member, the staple-shaped member comprising laterally spaced legs connected by a joining member;
(b) connecting a crimping device to said joining member; and,
(c) crimping said joining member in a direction generally transverse to a plane in which at least one of said legs extends.

26. A device for crimping a staple having a pair of laterally spaced legs connected by a central longitudinal member and the legs and the longitudinal member lying on a common plane, said device comprising:
(a) first means for engaging and supporting the staple so that the legs and the longitudinal member lie on a first common plane; and
(b) second means operably associated with said first means movable generally transverse to said first common plane and selectively engageable with the central longitudinal member for causing the member to be crimped on a second plane generally transverse to said first common plane for thereby causing the legs to approach each other.

27. The device of claim 26, wherein:
(a) said first means including first and second cooperating jaws;
(b) each of said first and second jaws including first and second laterally spaced jaw members defining therebetween a recess; and
(c) said second means movable in said recess.

28. The device of claim 27, wherein:
(a) each jaw member of one of said jaws includes a groove extending therethrough and the groves are coaxial.

29. The device of claim 28, wherein:
(a) said second means including a head portion having a groove disposed on the tip thereof;
(b) said head portion groove engageable with the central longitudinal member; and
(c) said coaxial grooves in said jaw members of said one of said jaws and said head portion groove being in general alignment with each other.

30. The device of claim 29, wherein:
(a) said first means including an adjustable fulcrum; and
(b) said second means movable on said fulcrum.

31. The device of claim 30, wherein:
(a) said second means including a generally planar lever arm lying on one side of said fulcrum and a head portion lying on the opposite side thereof; and
(b) means for pivoting said second means about said fulcrum.

32. The device of claim 31, wherein:
(a) said second means is slidable on said fulcrum.

33. The device of claim 32, wherein:
(a) said first jaw is pivotable relative to said first means.

34. The device of claim 33, and including:
(a) means operably associated with said first jaw for locking said first jaw in a preselected position.

35. The device of claim 34, wherein:
(a) said locking means is in general alignment with said pivoting means.

36. The device of claim 35, wherein:
(a) said first means including a pair of laterally spaced shoulders extending generally transverse to said jaws and defining therebetween a third recess.

37. The device of claim 36, wherein:
(a) said fulcrum and said pivot means are disposed in general alignment with said third recess and intermediate said shoulders.

38. A crimper, comprising:
(a) a staple having a pair of laterally spaced legs connected by a central longitudinal member and the legs and the central member lying on a common plane;
(b) first means engaging the central member thereby supporting the staple; and
(c) second means operably associated with said first means movable generally transverse to the common plane and selectively engaged with the central longitudinal member for causing the member to be crimped on a second plane generally transverse to the common plane for thereby causing the legs to approach each other.

39. The device of claim 38, wherein:
(a) said first means including first and second cooperating jaws;
(b) each of said first and second jaws including first and second laterally spaced jaw members defining therebetween a recess; and
(c) said second means movable in said recess.

40. The device of claim 39, wherein:
(a) each jaw member of one of said jaws includes a groove extending therethrough and the grooves are coaxial.

41. The device of claim 40, wherein:
(a) said second means including a head portion having a groove disposed on the tip thereof;
(b) said head portion groove engageable with the central longitudinal member; and
(c) said coaxial grooves in said jaw members of said one of said jaws and said head portion groove being in general alignment with each other.

42. The device of claim 41, wherein:
(a) said first means including an adjustable fulcrum; and
(b) said second means movable on said fulcrum.

43. The device of claim 42, wherein:
(a) said second means including a generally planar lever arm lying on one side of said fulcrum and a head portion lying on the opposite side thereof; and
(b) means for pivoting said second means about said fulcrum.

44. The device of claim 43, wherein:
(a) said second means is slidable on said fulcrum.

45. The device of claim 44, wherein:
(a) said first jaw is pivotable relative to said first means.

46. The device of claim 45, and including:
(a) means operably associated with said first jaw for locking said first jaw in a preselected position.

47. The device of claim 46, wherein:
(a) said locking means is in general alignment with said pivoting means.

48. The device of claim 47, wherein:
(a) said first means including a pair of laterally spaced shoulders extending generally transverse to said jaws and defining therebetween a third recess.

49. The device of claim 48, wherein:
(a) said fulcrum and said pivot means are disposed in general alignment with said third recess and intermediate said shoulders.

50. A device for crimping a staple having a pair of laterally spaced legs connected by a central longitudinal member and the legs and the longitudinal member lying on a common plane, said device comprising:
(a) first means for engaging and supporting the staple so that the legs and the longitudinal member lie on a first common plane;
(b) said first engaging means including first and second cooperating jaws;
(c) each of said first and second jaws including first and second laterally spaced jaw members defining therebetween a recess; and
(d) each jaw member of said one of said jaws including a groove extending therethrough and the grooves are coaxial and defining an axis about which the central longitudinal member is held; and
(e) second means operably associated with said first means movable in said recess generally perpendicular to said groove and selectively engageable with the central longitudinal member for causing the member to be crimped on a second plane generally transverse to said first common plane for thereby causing the legs to approach each other.

51. The device of claim 50, wherein:
(a) said first means including an adjustable fulcrum; and
(b) said second means movable on said fulcrum.

52. The device of claim 51, wherein:
(a) said second means including a head portion lying on one side of said fulcrum and a generally planar lever arm lying on the opposite side thereof.

53. The device of claim 52, wherein:

(a) said head portion including a generally transversely extending groove disposed at the tip thereof; and
(b) said head portion groove engageable with the central longitudinal member.

54. The device of claim 53, and including:
(a) means for pivoting said second means about said fulcrum being disposed on said lever arm.

55. The device of claim 54, wherein:
(a) said pivoting means including a screw means;
(b) said lever arm including a screw-threaded hole for receiving said screw means; and
(c) a portion of said screw means engageable with a corresponding portion of said first means such that when said screw means is tightened said second means pivots about said fulcrum.

56. The device of claim 55, wherein:
(a) said first jaw is pivotable relative to said first means.

57. The device of claim 56, and including:
(a) means operably associated with said first jaw for locking said first jaw in a preselected position.

58. The device of claim 57, wherein:
(a) said locking means is in general alignment with said pivoting means.

59. The device of claim 58, wherein:
(a) said first means including a pair of laterally spaced shoulders extending generally transverse to said jaws and defining therebetween a third recess.

60. The device of claim 59, wherein:
(a) said fulcrum and said pivot means are disposed in general alignment with said third recess and intermediate said shoulders.

* * * * *